United States Patent
Rasmussen et al.

(10) Patent No.: US 7,377,915 B2
(45) Date of Patent: May 27, 2008

(54) CATHETER CONNECTOR SYSTEM

(75) Inventors: Kelly Rasmussen, Orem, UT (US);
Jeffrey K. Anderson, Provo, UT (US);
Jack R. Peterson, Orem, UT (US);
David W. Pierce, Provo, UT (US);
Scott D. Hinckley, Farmington, UT (US); Abraham C. Teng, Orem, UT (US); William R. Barron, Riverton, UT (US); Catherine C. Breiter, Holladay, UT (US)

(73) Assignee: C. R. Bard, Inc., Murray Hill, NJ (US)

( * ) Notice: Subject to any disclaimer, the term of this patent is extended or adjusted under 35 U.S.C. 154(b) by 0 days.

(21) Appl. No.: 11/096,553

(22) Filed: Apr. 1, 2005

(65) Prior Publication Data
US 2006/0015086 A1    Jan. 19, 2006

Related U.S. Application Data

(60) Provisional application No. 60/558,150, filed on Apr. 1, 2004.

(51) Int. Cl.
*A61M 25/00* (2006.01)
(52) U.S. Cl. ...................................... 604/523
(58) Field of Classification Search ................. 604/43, 604/535, 284, 534, 533, 27, 29, 264, 256, 604/167.01, 164.04, 523, 536, 538, 539, 604/175
See application file for complete search history.

(56) References Cited

U.S. PATENT DOCUMENTS

| | | | |
|---|---|---|---|
| 3,572,340 A | 3/1971 | Lloyd et al. ................ 65/181 |
| 3,650,507 A | 3/1972 | Nyberg .................... 251/149.6 |
| 4,029,095 A | 6/1977 | Pena ........................... 604/30 |
| 4,112,949 A | 9/1978 | Rosenthal et al. ........... 604/319 |
| 4,490,003 A | 12/1984 | Robinson ..................... 439/325 |
| 4,675,020 A | 6/1987 | McPhee ..................... 604/411 |
| 4,772,268 A * | 9/1988 | Bates ......................... 604/174 |
| 4,850,955 A | 7/1989 | Newkirk ....................... 604/9 |
| 5,053,004 A | 10/1991 | Markel et al. |
| 5,112,323 A | 5/1992 | Winkler et al. ............. 604/319 |
| 5,137,524 A | 8/1992 | Lynn et al. ................. 604/533 |
| 5,251,873 A | 10/1993 | Atkinson et al. ........ 251/149.1 |
| 5,312,337 A * | 5/1994 | Flaherty et al. ............. 285/278 |
| 5,401,245 A | 3/1995 | Haining ....................... 604/86 |
| 5,484,401 A | 1/1996 | Rodriguez et al. ........... 604/28 |
| 5,496,299 A | 3/1996 | Felix et al. ................ 604/319 |
| 5,507,733 A | 4/1996 | Larkin et al. ............... 604/534 |
| 5,514,117 A | 5/1996 | Lynn ......................... 604/536 |

(Continued)

FOREIGN PATENT DOCUMENTS

EP        0439263        7/1991

(Continued)

*Primary Examiner*—Nicholas D. Lucchesi
*Assistant Examiner*—Christopher D Koharski
(74) *Attorney, Agent, or Firm*—Stoel Rives LLP

(57) ABSTRACT

A catheter connector system that allows trimming of the proximal end of a catheter (single or multiple lumen) prior to the placement of a connector hub. In one variation, the catheter connector system comprises a catheter, a connector sheath including a soft collet, and a connector hub including a cannula for engaging the catheter and a connector hub interface for receiving the connector sheath.

19 Claims, 7 Drawing Sheets

U.S. PATENT DOCUMENTS

| | | | |
|---|---|---|---|
| 5,520,665 A | 5/1996 | Fleetwood | 604/537 |
| 5,556,387 A | 9/1996 | Mollenauer et al. | 604/249 |
| 5,624,413 A | 4/1997 | Markel et al. | |
| 5,636,875 A | 6/1997 | Wasser | 285/21.1 |
| 5,637,102 A * | 6/1997 | Tolkoff et al. | 604/536 |
| 5,718,678 A | 2/1998 | Fleming, III | |
| 5,718,692 A | 2/1998 | Schon et al. | |
| 5,725,506 A | 3/1998 | Freeman et al. | 604/167.1 |
| 5,776,111 A | 7/1998 | Tesio | |
| 5,947,953 A | 9/1999 | Ash et al. | |
| 5,997,486 A | 12/1999 | Burek et al. | 600/573 |
| 6,068,011 A | 5/2000 | Paradis | 137/1 |
| 6,074,379 A | 6/2000 | Prichard | 604/524 |
| 6,093,154 A | 7/2000 | Burek et al. | 600/564 |
| 6,106,503 A | 8/2000 | Pfeiderer et al. | 604/246 |
| 6,132,407 A | 10/2000 | Genese et al. | 604/327 |
| 6,190,349 B1 | 2/2001 | Ash et al. | |
| 6,423,053 B1 * | 7/2002 | Lee | 604/533 |
| 6,626,418 B2 | 9/2003 | Kiehne | 251/149.6 |
| 6,638,242 B2 * | 10/2003 | Wilson et al. | 604/43 |
| 6,641,574 B2 | 11/2003 | Badia Segura | 604/533 |
| 6,669,681 B2 | 12/2003 | Jepson et al. | 604/533 |
| 6,682,519 B1 | 1/2004 | Schon | |
| 6,695,832 B2 | 2/2004 | Schon et al. | |
| 6,719,749 B1 | 4/2004 | Schweikert et al. | |
| 6,872,198 B1 | 3/2005 | Wilson et al. | |
| 6,881,211 B2 | 4/2005 | Schweikert et al. | |
| D505,202 S | 5/2005 | Chesnin | |
| 6,916,051 B2 | 7/2005 | Fisher | |
| 6,921,396 B1 | 7/2005 | Wilson et al. | |
| 6,969,381 B2 * | 11/2005 | Voorhees | 604/534 |
| 7,044,441 B2 | 5/2006 | Doyle | 251/149.6 |
| 7,048,724 B2 | 5/2006 | Grossman et al. | 604/319 |
| 7,163,531 B2 | 1/2007 | Seese et al. | |
| 7,182,746 B2 | 2/2007 | Haarala et al. | |
| 7,258,685 B2 | 8/2007 | Kerr | |
| 7,300,430 B2 | 11/2007 | Wilson et al. | |
| 2002/0010437 A1 * | 1/2002 | Lopez et al. | 604/256 |
| 2004/0065333 A1 | 4/2004 | Wilson et al. | |
| 2004/0082923 A1 | 4/2004 | Field | 604/267 |
| 2004/0092863 A1 | 5/2004 | Raulerson et al. | |
| 2004/0097903 A1 | 5/2004 | Raulerson | |
| 2004/0122418 A1 | 6/2004 | Voorhees | |
| 2004/0171997 A1 | 9/2004 | Wilson et al. | |
| 2004/0172003 A1 | 9/2004 | Wilson et al. | |
| 2005/0080398 A1 | 4/2005 | Markel et al. | |
| 2005/0085765 A1 | 4/2005 | Voorhees | |
| 2005/0085794 A1 | 4/2005 | Denoth et al. | |
| 2005/0095891 A1 | 5/2005 | Schorn | |
| 2005/0096585 A1 | 5/2005 | Schon et al. | |
| 2005/0187535 A1 | 8/2005 | Wilson et al. | |
| 2005/0209572 A1 | 9/2005 | Rome et al. | 604/250 |
| 2005/0209581 A1 * | 9/2005 | Butts et al. | 604/523 |
| 2005/0261636 A1 | 11/2005 | Rome et al. | 604/247 |
| 2005/0261664 A1 | 11/2005 | Rome et al. | 604/508 |
| 2005/0261665 A1 | 11/2005 | Voorhees | 604/508 |
| 2006/0015086 A1 | 1/2006 | Rasmussen et al. | 604/533 |
| 2006/0276773 A1 | 12/2006 | Wilson et al. | 604/523 |
| 2007/0016167 A1 | 1/2007 | Smith et al. | |
| 2007/0060866 A1 | 3/2007 | Raulerson et al. | |
| 2008/0009832 A1 | 1/2008 | Barron et al. | |

FOREIGN PATENT DOCUMENTS

| | | |
|---|---|---|
| WO | WO8401902 | 5/1984 |
| WO | WO2006004943 | 1/2006 |
| WO | WO2006066023 | 6/2006 |
| WO | WO 2006/130133 A1 | 12/2006 |

\* cited by examiner

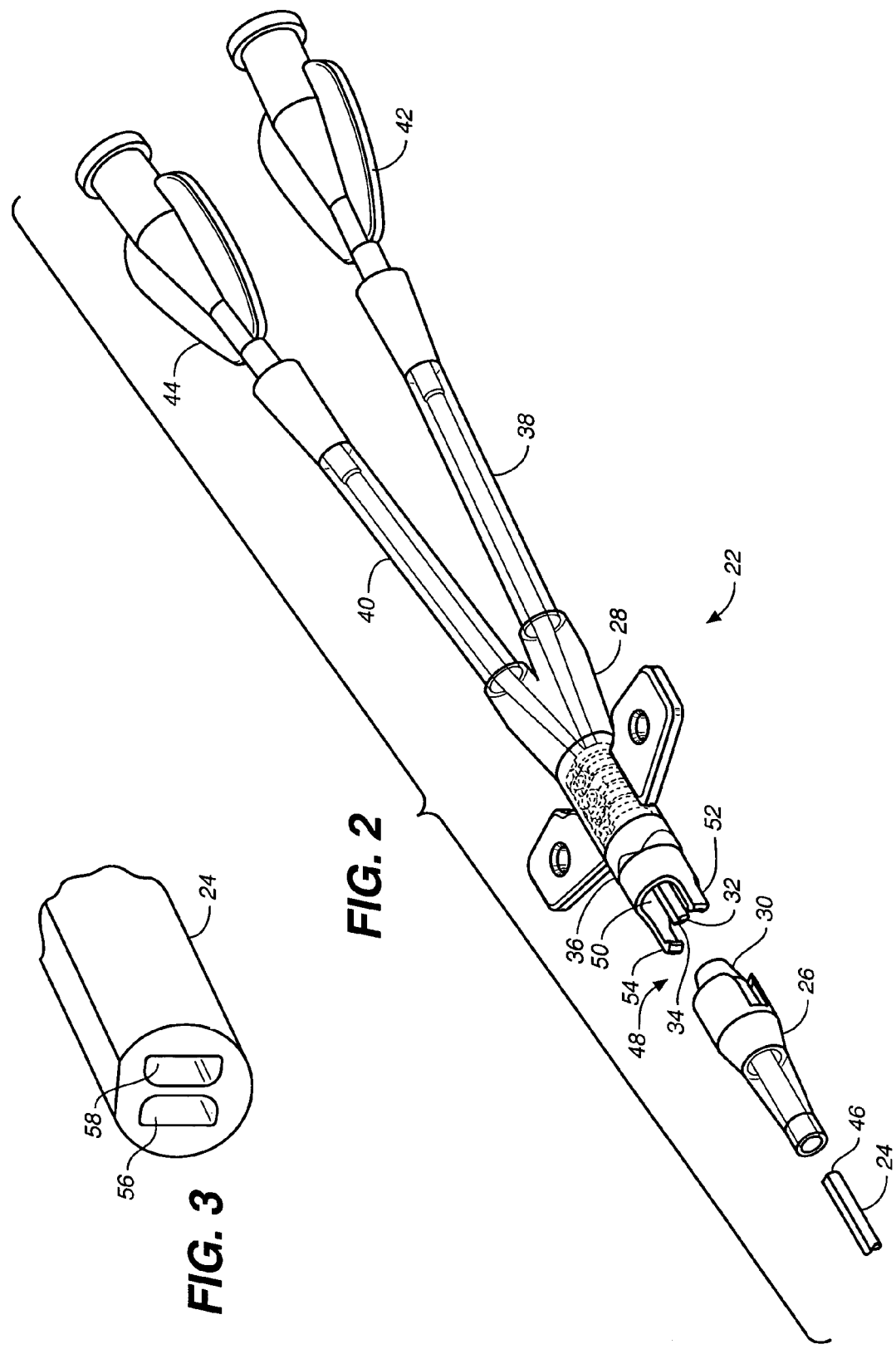

CATHETER CONNECTOR SYSTEM

CROSS-REFERENCE TO RELATED APPLICATIONS

This application claims the benefit of U.S. Provisional Application No. 60/558,150, entitled "CATHETER CONNECTOR SYSTEM," filed Apr. 1, 2004, which is incorporated herein by reference in its entirety.

STATEMENT REGARDING FEDERALLY SPONSORED RESEARCH OR DEVELOPMENT

Not applicable.

REFERENCE TO A COMPACT DISK APPENDIX

Not applicable.

BACKGROUND OF THE INVENTION

It is common to use an implanted catheter to repeatedly access the vascular system of a patient and with the catheter perform repeated therapeutic medical activity. Such therapeutic activity could include the intermittent or continuous infusion of medication and fluids, the periodic sampling of blood, or the continuous withdrawal and return of blood for processing outside of the body of the patient. The catheters used in these activities are referred to as vascular access catheters.

Before any therapeutic activity can actually commence, however, the vascular access catheter must be implanted in the body of the patient with the distal tip of the catheter residing at the location in the vascular system at which an intended therapeutic activity is appropriate. Typically, most of the length of an implanted vascular access catheter resides within blood vessels of the vascular system, extending from the distal tip of the catheter to a location in the vascular system at which the catheter, by traversing a puncture or incision formed through a wall of the blood vessel in which the catheter is disposed, enters into the surrounding subcutaneous tissue of the patient. The location at which this occurs is referred to as a venipuncture site. Venipuncture sites are classified on the basis of the position of a venipuncture site in relation to the center of the body of the patient. Central venipuncture sites are those that enter the vasculature through the jugular or subclavian veins. Peripheral venipuncture sites typically enter the basilic or cephalic veins of the upper or lower arm. The freedom to select among venipuncture sites is determined largely on catheter size and vein size. Vein size is dependent on patient size and on location within the body, with peripheral veins being smaller than central veins.

Proximal of the venipuncture site, the implanted catheter extends through the subcutaneous tissue of the patient to emerge through the skin at a location that is referred to as the skin exit site. Most skin exit sites are chosen as being locations at which the proximal end of the implanted catheter can be easily manipulated by medical personnel. Favored among such locations are the neck, the region about the collar bone or chest wall, the upper leg, the upper arm, and the forearm. Occasionally, the skin exit site is somewhat removed from the venipuncture site. Then, a significant portion of the length of the implanted catheter must be embedded in the subcutaneous tissue of the patient in a surgically created tunnel that extends from the venipuncture site to the skin exit site. In all instances, a portion of the proximal end of an implanted catheter must remain outside of the body of the patient. It is this portion of an implanted catheter, from the proximal end thereof to the skin access site that is referred to as the extracorporeal portion of the implanted catheter.

In various applications, the extracorporeal portion of an implanted catheter needs to be configured to permit selective coupling and uncoupling between the tubing and the medical equipment outside the body of the patient that are required for therapeutic activity. Accordingly, the proximal end of the vascular access catheters is configured to terminate in a catheter coupling hub that can be secured in fluid communication with such tubing and medical equipment, or can be capped, valved, or clamped closed between periods of actual use. Due to the variation in length of catheter that is required to traverse the subcutaneous and intravascular route from implanted tip location to skin exit site, it often becomes necessary to trim the catheter to an appropriate length. Traditionally, it is the distal end of the catheter that is trimmed.

Trimming the catheter to an appropriate length is particularly advantageous with respect to Peripherally Inserted Central Catheters (PICCs) where precise central venous catheter tip placement at the right atrial (RA), superior vena cava (SVC) junction is imperative to prevent potential thrombosis, traumatic or functional complications. Many types of catheters, however, cannot be distally trimmed due to the special configuration thereof, including, for example, dual lumen catheters with a pre-staggered tip, soft tip catheters, catheters with valved distal ends, etc. In the case of such catheters, a pre-connected hub at the proximal end of the catheter cannot be accurately located at the venipuncture site and, consequently, some length of catheter extends there from. This excess catheter length often presents difficulty in dressing the catheter and exposes the catheter to potential damage.

Whether or not the catheter has a preformed distal tip, it is advantageous to be able to trim a catheter at its proximal end prior to connection to a coupling hub or other extracorporeal medical equipment because proximal trimming may allow the physicians to keep inventory low (as several different catheter lengths are unnecessary), and each catheter implanted can be customized to the exact length optimal for patient comfort and operability of the catheter. Therefore, a catheter connector system that permits the proximal end of a catheter to be trimmed and allows coupling of a connector hub to the trimmed proximal end for repeated access of the catheter may desirable in various medical applications.

SUMMARY OF THE INVENTION

The present invention is directed to a catheter connector system for a subcutaneously-placed catheter. Accordingly, it is an embodiment of the present invention to provide a catheter connector system, which safely and effectively connects a proximal end of a catheter to extracorporeal medical device/equipment, following placement of the distal end of the catheter in a patient. It is a further embodiment of the present invention to provide a catheter connector system that reduces assembly time of an associated suture wing, provides the functionality of a repair kit, and/or provides a proximally trimmable design for a multi-lumen catheter.

In one variation, the catheter connection system comprises a dual lumen catheter, a bifurcation, and a connector sheath for securing the proximal end of the dual lumen catheter to the bifurcation. The connector sheath comprises a proximally extending collet and a distally extending strain relief. The distal end of the bifurcation comprises an interface including two cannulas for insertion into the lumens of the dual lumen catheter, a cavity surrounding the cannulas being configured for receiving the collet on the connector sheath, and a locking element for securing the connector sheath to the bifurcation. To attach the catheter to the bifurcation, the proximal end of the catheter is passed through the lumen of the connector sheath and placed over the cannulas (i.e., with the cannulas inserted within the lumens of the catheter). The connector sheath is then displaced proximally to engage the distal interface of the bifurcation. When the connector sheath is coupled to the bifurcation, the collet is inserted within the cavity at the distal interface and the inner wall of the cavity forces the collet onto the proximal portion of the catheter and secures the catheter to the bifurcation. In one design variation, the collet comprises a pliable polymeric material. In another design variation, each of the two cannulas comprises non-circular circumferential surface. In yet another design variation, each of the two catheter lumens comprises a D-shaped cross-section.

These and other embodiments, features and advantages of the present invention will become more apparent to those skilled in the art when taken with reference to the following more detailed description of the invention in conjunction with the accompanying drawings that are first briefly described.

BRIEF DESCRIPTION OF THE DRAWINGS

FIG. 2 illustrates one variation of a catheter connector system comprising a connector sheath for securing a dual lumen catheter to a corresponding bifurcation. In this design, the proximal end of the catheter can be trimmed before it is coupled to the bifurcation.

FIG. 3 shows one variation of a dual-lumen catheter with D-shaped lumens.

FIGS. 9-12 illustrates one method for utilizing a connector sheath to connect a dual lumen catheter to a bifurcation.

FIG. 9 shows a dual lumen catheter, a bifurcation, and a corresponding connector sheath in a disassembled condition.

FIG. 10 illustrates the connector sheath being slid on to the shaft of the catheter.

FIG. 12 illustrates the connector sheath being displaced in the proximal direction and coupled to the distal interface on the bifurcation.

DETAILED DESCRIPTION OF THE INVENTION

Figure 1:
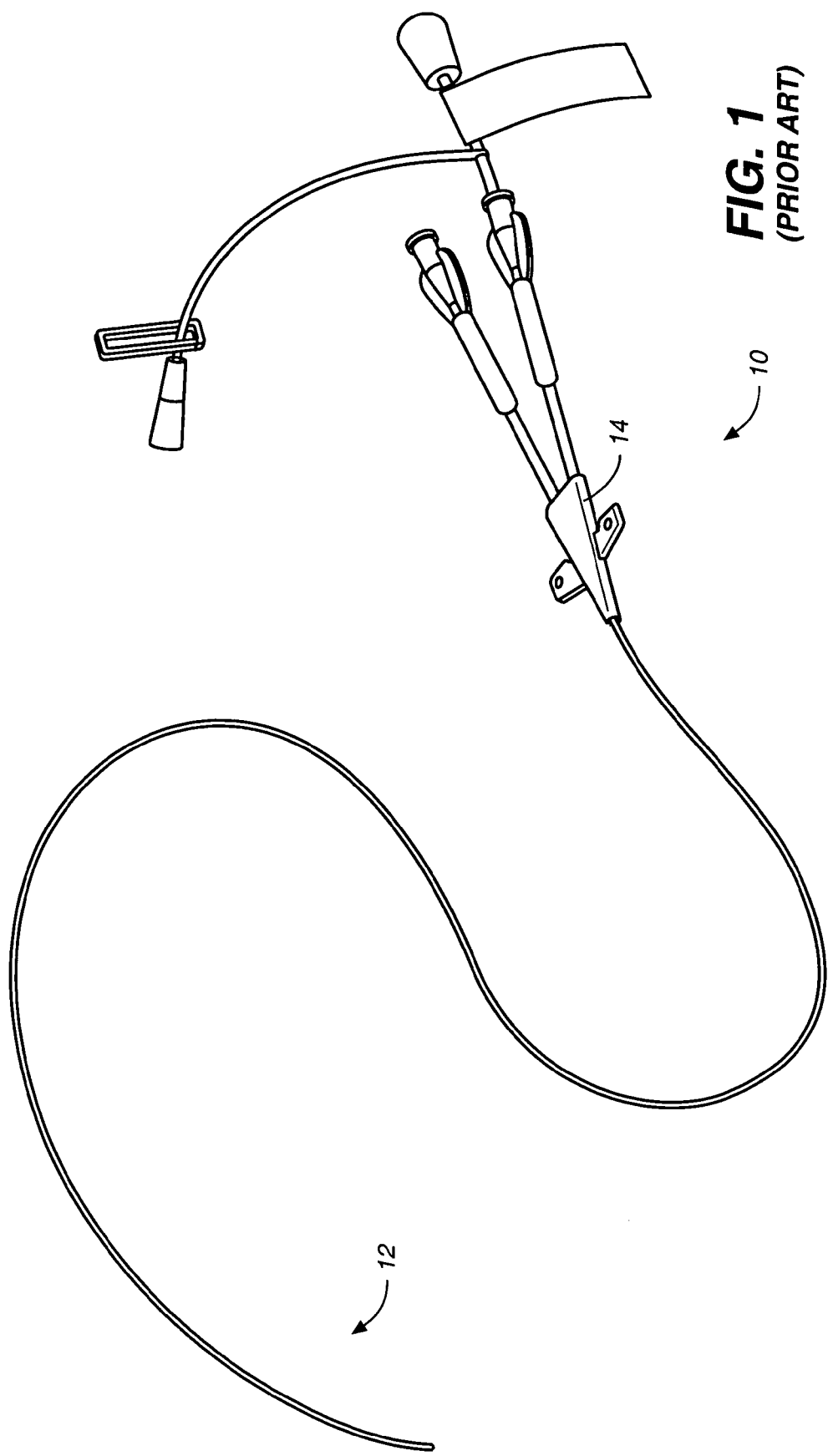
FIG. 1 shows a fixed length prior art dual lumen peripherally inserted central catheter that cannot be trimmed.

The following detailed description should be read with reference to the drawings, in which identical reference numbers refer to like elements throughout the different figures. The drawings, which are not necessarily to scale, depict selective embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

Before describing the present invention, it is to be understood that unless otherwise indicated this invention need not be limited to applications in humans. As one of ordinary skill in the art would appreciate, variations of the invention may be applied to other mammals as well. Moreover, it should be understood that embodiments of the present invention may be applied in combination with various catheters, tubing introducers or other catheter implantation and connection devices for establishing a fluid conduit into a patient's body.

Establishment of a central line utilizing a Peripherally Inserted Central Catheter (PICC) is used herein as an example application of the catheter connector system to illustrate the various aspects of the invention disclosed herein. In light of the disclosure herein, one of ordinary skill in the art would appreciate that variations of the catheter connector system may be utilized in various medical procedures for establishing a fluid conduit into a patient's body. Although the catheter connector system may be particularly useful in catheter implantation that requires reverse tunneling, it is also contemplated that the catheter connector system can be utilized in various catheter implant procedures that do not require reverse tunneling.

It must also be noted that, as used in this specification and the appended claims, the singular forms "a," "an" and "the" include plural referents unless the context clearly dictates otherwise. Thus, for example, the term "a snap-lock arm" is intended to mean a single snap-lock arm or a combination of snap-lock arms, "a fluid" is intended to mean one or more fluids, or a mixture thereof. Furthermore, the words "proximal" and "distal" refer to directions closer to and away from, respectively, a physician operating the device, with the tip end (i.e., distal end) placed inside the patient's body. Thus, for example, the catheter end placed within the body of the patient would be the distal end of the catheter, while the catheter end outside the patient's body would be the proximal end of the catheter. In addition, the term "soft" as used herein means pliable or compressible. The term "hard" as used herein means rigid. Preferably, a soft material has a Durometer measurement of less than about 100 Shore A, and a hard material has a Durometer measurement of more than about 100 Shore A. For example, in one variation the hard material implemented in a catheter connector system includes materials with a hardness of at least 60 Shore D. Moreover, the term "unitary piece" as used herein means a single functional component that may comprise one or more interconnecting parts coupled together.

This invention is directed to a catheter connection system for securing a single or multi-lumen catheter to a connection hub. In particular, the various designs disclosed herein allow the physician to trim the catheter to length to fit the patient's body sizes prior to establishing a connection interface with the connection hub. In one variation, a connector sheath is disposed over the distal portion of the catheter to serve as a compression interface. The distal portion of the connector hub is configured to apply an inwardly directed force on the proximal portion of the connector sheath, such that the connector sheath grips around the circumference of the catheter and secures the catheter on the connector hub's cannula, which is inserted within the lumen of the catheter.

The catheter connection system allows the physician to trim the proximal end of the catheter to the desired length before establishing a connection hub on the proximal end of the catheter. This design allows the physician to customize the length of the catheter to meet the requirements of the particular medical procedure and modify the catheter according to the deployment location and the patient's physical size. In comparison, an existing fixed-length dual lumen catheter 10, such as the one shown in FIG. 1, cannot be trimmed due to valves in the distal end 12 and a bifurcation 14 permanently connected to the proximal end.

In one variation, the trimmable single or multi-lumen catheter is configured with a valve (e.g., Groshong® valve, etc.) at the distal end, and a bifurcation at the proximal end, but the bifurcation could be detached (i.e., not molded on during the manufacturing process). In one particular design, the catheter is configured to serve as a Peripherally Inserted Central Catheter (PICC) line. The distal portion of the catheter can be inserted into the patient's body first. Once the distal end of the catheter is positioned in place, the catheter is trimmed to length at the proximal end, after which, the bifurcation is attached. The catheter may be comprised of one or more polymers that are well known to one of ordinary skill in the art. In one variation, the catheter comprises silicone, while in another variation, the catheter comprises polyurethane.

In one example, the catheter connector system 22 comprises a dual lumen catheter 24, a connector sheath 26, and a bifurcation 28 (i.e., connector hub), as shown in FIG. 2. The connector sheath comprises a soft collet 30 which extends proximally. The bifurcation 28 comprises two cannulas 32, 34, and an overmold 36. Two extension legs 38, 40 are connected to the proximal ends of the two cannulas 32, 34. Luer connectors 42, 44 are provided over the proximal end of the extension legs 38, 40. The distal ends of the cannula 32, 34 are configured for insertion into the lumens at the proximal end 46 of the catheter 24. The distal end of the bifurcation 28 is configured with an interface 48 for receiving the proximal end of the connector sheath 26. The distal interface 48 includes a cavity 50 for receiving at least portion of the soft collet 30, such that when the soft collet is inserted within the cavity, the inner wall of the cavity compresses the soft collet inwardly towards a center region of the cavity. The distal interface 48 also includes two locking elements 52, 54, which extend distally for engaging and securing the connector sheath 26 to the bifurcation 28.

Figure 4:
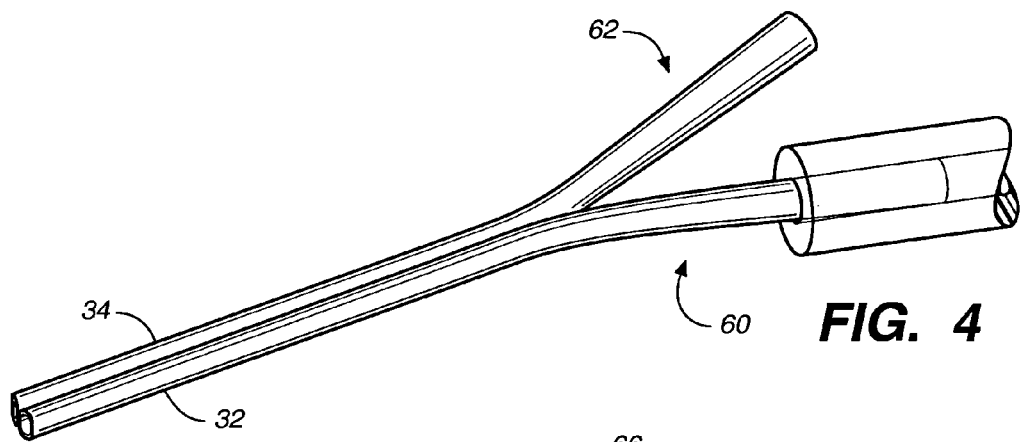
FIG. 4 illustrates one design variation where two cannulas are configured to form a bifurcation.

In one variation, each of the cannulas comprises a metal tubing. The outer circumferential surface of the cannula is configured to match the inner wall of the catheter lumen, such that when the cannula is inserted within the catheter lumen, a seal is established. In one example, the catheter lumens 56, 58 are configured with D-shaped cross-sections as shown in FIG. 3. The cannulas 32, 34 are configured with corresponding D-shaped cross-sections, as shown in FIG. 4, which provide a good seal with the catheter and permit the insertion of the cannula into the proximal end of the catheter without the use of a core pin. Moreover, the combination of a metal material and tailored cross-sectional shapes impart the ability of the connector system to support a high burst pressure of at least about 100 psi. Furthermore, as shown in FIG. 4, in this particular design, the proximal portions 60, 62 of the cannulas are configured such that they angle away from each other. In one variation, the lumen within the distal portion of each of the cannula is configured to expand gradually from the bifurcating point towards the proximal end of the cannula, to provide a smooth fluid flow transition between the proximal end with a large cannula opening and the distal end with a smaller cannula opening (in comparison with the proximal opening). This design allows one to direct fluid from an extension leg with a larger lumen into a catheter with a smaller lumen.

The catheter connector system 22 can be configured to support a specific minimum pull-off force (the force to pull the catheter tube off of the connector hub or attachment) requirement, such that accidental removal of the connection hub may be prevented. In one variation, the connector system is configured with a minimum pull-off force of about 3.37 lbs. or higher. In another variation, the connector system is configured with a minimum pull-off force of about 4 lbs. or higher.

Figure 5A:
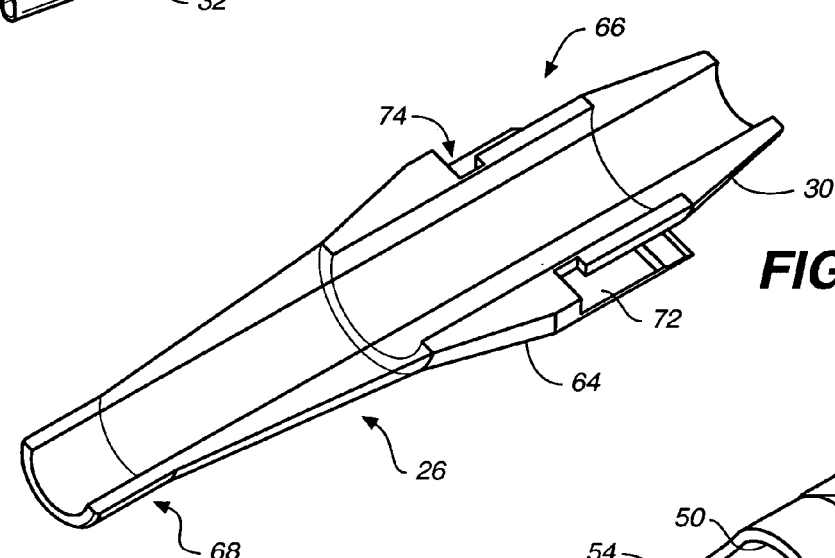
FIG. 5A illustrates one variation of a connector sheath.
Figure 5B:
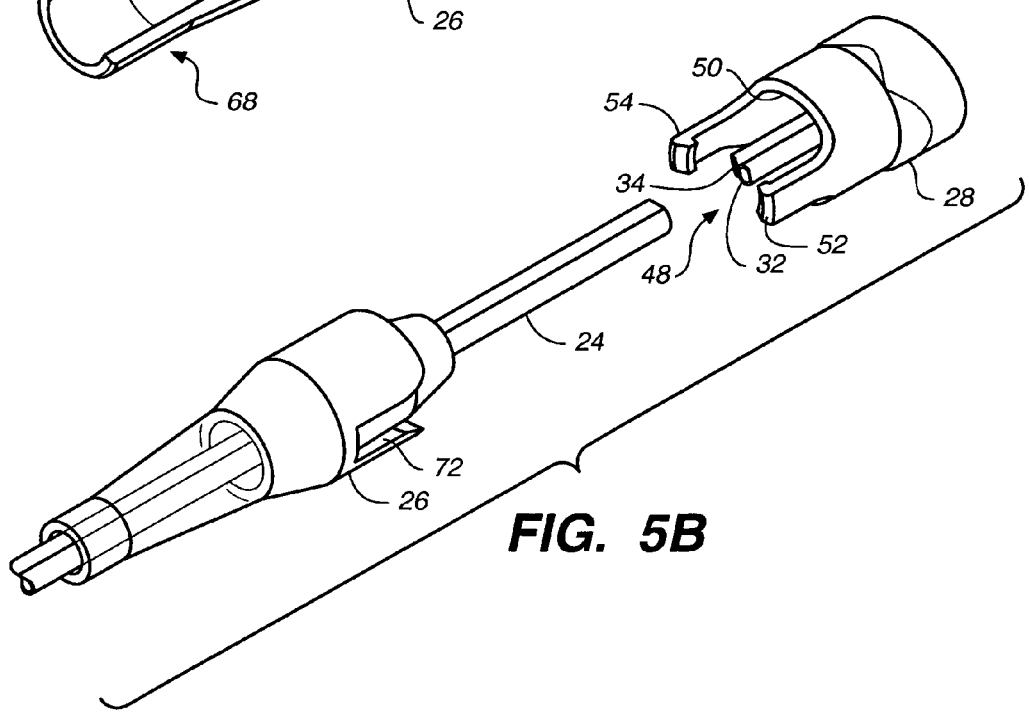
FIG. 5B shows the connector sheath of FIG. 5A slidably disposed over the shaft of a dual lumen catheter prior to coupling the proximal end of the catheter to a distal end of a corresponding bifurcation. The distal interface of the corresponding bifurcation is also shown.

FIG. 5A illustrates one variation of a connector sheath 26. The connector sheath comprises a soft collet 30 and a collet-sheath 64 positioned around the soft collet 30. In this particular design, the soft collet 30 comprises a short segment of a pliable polymeric tube, with the proximal end 66 extending past the collet-sheath 64 and configured to engage the distal interface 48 of the bifurcation 28. The distal portion 68 of the soft collet also extends beyond the collet-sheath. The distal portion 68 of the soft collet 30 is configured to serve as strain relief. In one variation, the collet-sheath 64 comprises a hard over-sheath.

Figure 6:
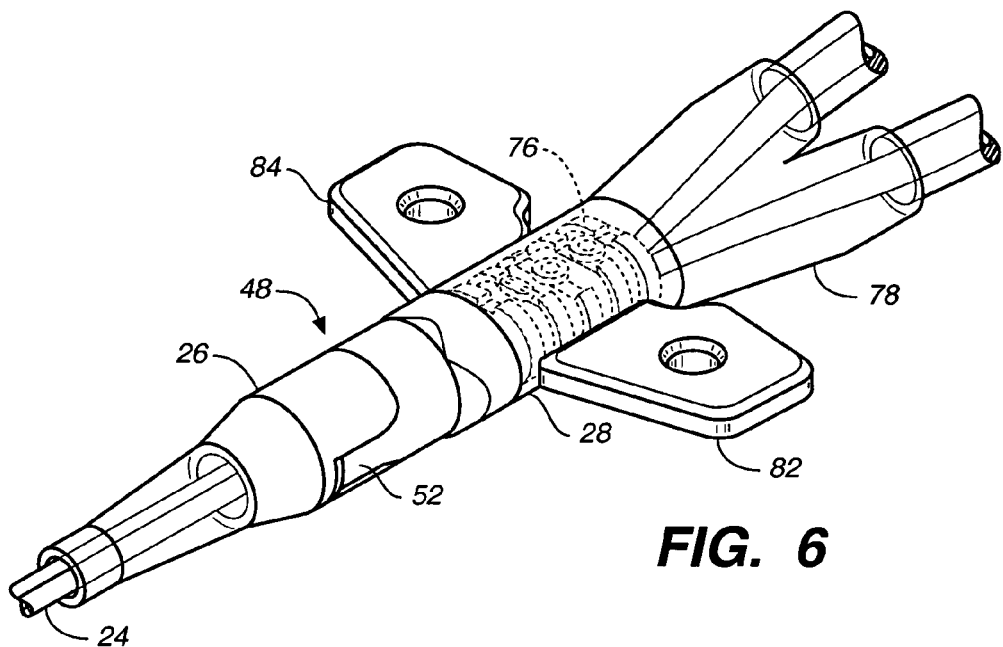
FIG. 6 shows the dual lumen catheter of FIG. 5B connected to its corresponding bifurcation. The connector sheath is coupled to the distal interface of the bifurcation to secure the proximal end of the catheter to the bifurcation.

To connect the catheter 24 to the bifurcation 28, the connector sheath 26 is first slidably positioned over a proximal end of the shaft of the catheter 24. Next, the proximal end of the catheter is placed over the distally extending cannulas 32, 34. When the cannulas are inserted within the lumens of the catheter, the outer diameter of the catheter tube may increase. The user then advances the connector sheath 26 in the proximal direction over the cannula/catheter connection, and continues the displacement until the locking elements 52, 54 (i.e., two prong arms) snap into the corresponding slots 72, 74 on the connector sheath 26, as shown in FIG. 6.

In this example, the distal interface 48 of the bifurcation 28 comprises a conical-shaped cavity 50. When the proximal end of the connector sheath is inserted into the conical-shaped cavity, the soft collet at the proximal end of the connector sheath is compressed, which in turn compresses the catheter tube evenly over the cannula. This compression force maintains the connection between the catheter and the bifurcation. Furthermore, with the prong arms snapped into the hard over-sheath of the connector sheath, the connector sheath is secured onto the distal end of the bifurcation. The presence of the locking elements (e.g., prong arms, snap-lock arms, etc.) increases the minimum force required to pull-off the connectors sheath to detach the catheter from the bifurcation.

In one variation, the distal interface 48 of the bifurcation 28 comprises a hard plastic material, such that the pliable polymeric collet inserted therein is compressed inwardly toward a longitudinal axis of the bifurcation as the collet engages the incline plane on the inner wall of the cavity. In addition, the hard over-sheath of the connector sheath 64 may also comprise a hard plastic material such that as the prong arms 52, 54 on the bifurcations distal interface engage the hard over-sheath 64, an audible click sound is created to notify the user of successful attachment. In one design configuration, the catheter connector system is configured with a burst pressure of at lease about 60 psi, a pull-off force of at least about 3.37 lbs., and an audible connection indicator sound level of at least about 60 dB. In another design configuration, the catheter connector system is configured with a burst pressure of at least about 100 psi, a pull-off force of at least about 4 lbs., and an audible connection indicator sound level of at least about 65 dB.

One of ordinary skill in the art having the benefit of this disclosure would appreciate that various methods that are well known to one of ordinary skill in the art may be utilized to fabricate the catheter connector system described herein. In one approach, a mold is manufactured to shape cannula tubings. Channels of a specific size are end-milled into a block of hardened aluminum. These channels with a specific width and depth are utilized to facilitate the compression of the cannulas. In one variation, the channels of the mold are rectangular in shape. When a round cannula is pressed into the channel, the cannula tubing is formed into a shape resembling a rectangle with rounded corners. This shape is substantially the same as the shape of a D-shaped lumen of the catheter tubing, which facilitates the insertion of the cannula into the D-shaped lumen and provides a good seal against fluid leakage at the junction between the cannula and the catheter.

Figure 7:
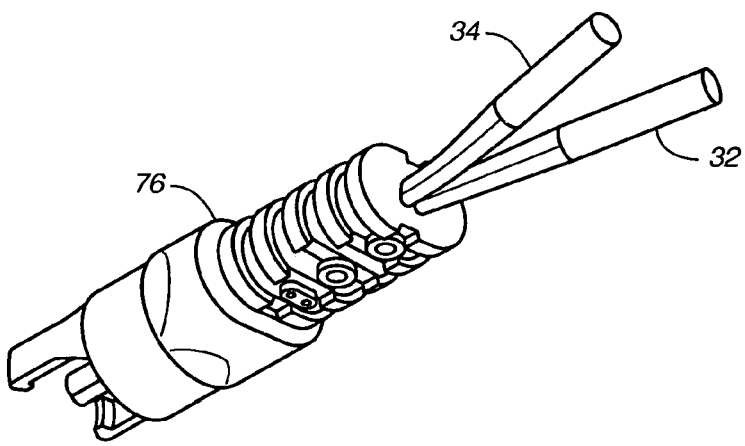
FIG. 7 illustrates a hard core overmolded over two cannulas during the formation of the bifurcation.

In one variation, the bifurcation comprises two cannulas 32, 34, a hard core 76 securing the two cannulas 32, 34, and a soft overmold 78. FIG. 7 shows a hard core 76 injection molded onto the two cannulas 32, 34 to secure the two cannulas 32, 34 in place. In one variation the hard core comprises an isoplast material. For example, the hard core may comprise of an isoplast material with a Durometer of about 121 Shore R. In another variation, the hard core comprises Valox®. For example, the hard core may comprise Valox® of about 118 Shore R. In another variation, the hard core comprises PVC (Poly Vinyl Chloride). For example, the hard core may comprise PVC of about 70-113 Shore R. Once the hard core is put in place, a soft overmold 78 is then injection molded over the hard core 76 and forms the bifurcation 28 shown in FIG. 6. Optionally, flexible polymeric wings 82, 84 may be overmolded onto the bifurcation during the manufacturing process. These wing members provide a mean of securing the catheter to the skin of the patient to ensure that potential tensile forces are applied to the connection assembly, and not the soft catheter material. In one variation, the soft overmold comprises a polymer of about 60 to about 100 Shore A. For example, the soft overmold may comprise polyurethane. In another variation, the soft overmold comprises a polymer of about 90 Shore A.

Figure 8:
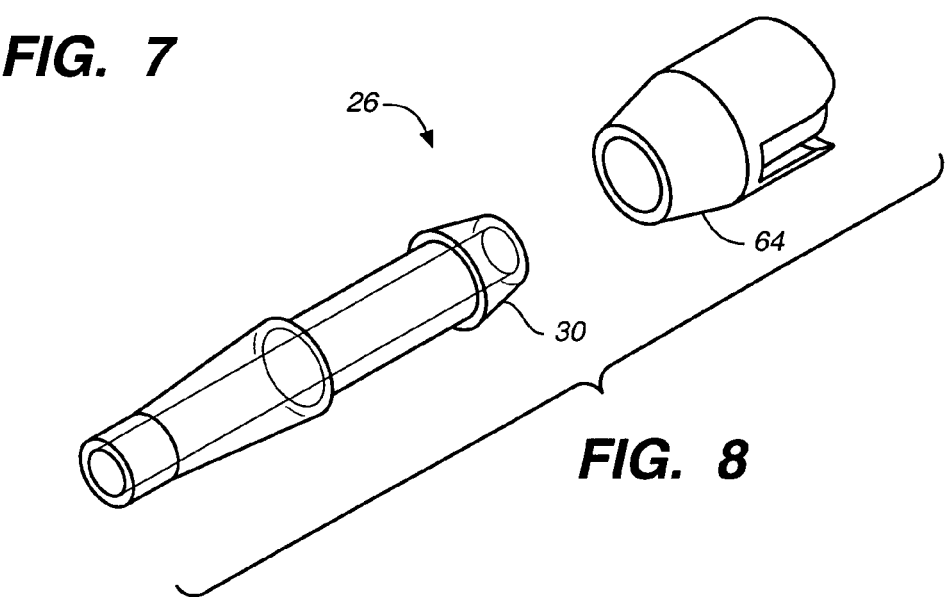
FIG. 8 illustrates one variation of a connector sheath comprising a hard over-sheath and a soft inner tubing. The hard over-sheath and the soft inner tubing are shown separated from each other. The proximal end of the soft inner tubing comprises a soft collet.

As discussed herein, in one variation, the connector sheath 26 is manufactured into a single functional piece. In one design, the soft collet 30, which serves as a compression member, is inserted into a hard over-sheath 64 during the manufacturing process to form a single piece connector sheath, as shown in FIG. 8. In one variation, the hard over-sheath comprises an isoplast material. In another variation, the hard over-sheath comprises Valox®. In another variation, the hard over-sheath comprises PVC (poly vinyl chloride). In yet another variation, the hard over-sheath comprises a polymer with a Durometer measurement of at least 100 Shore A.

Figure 9:
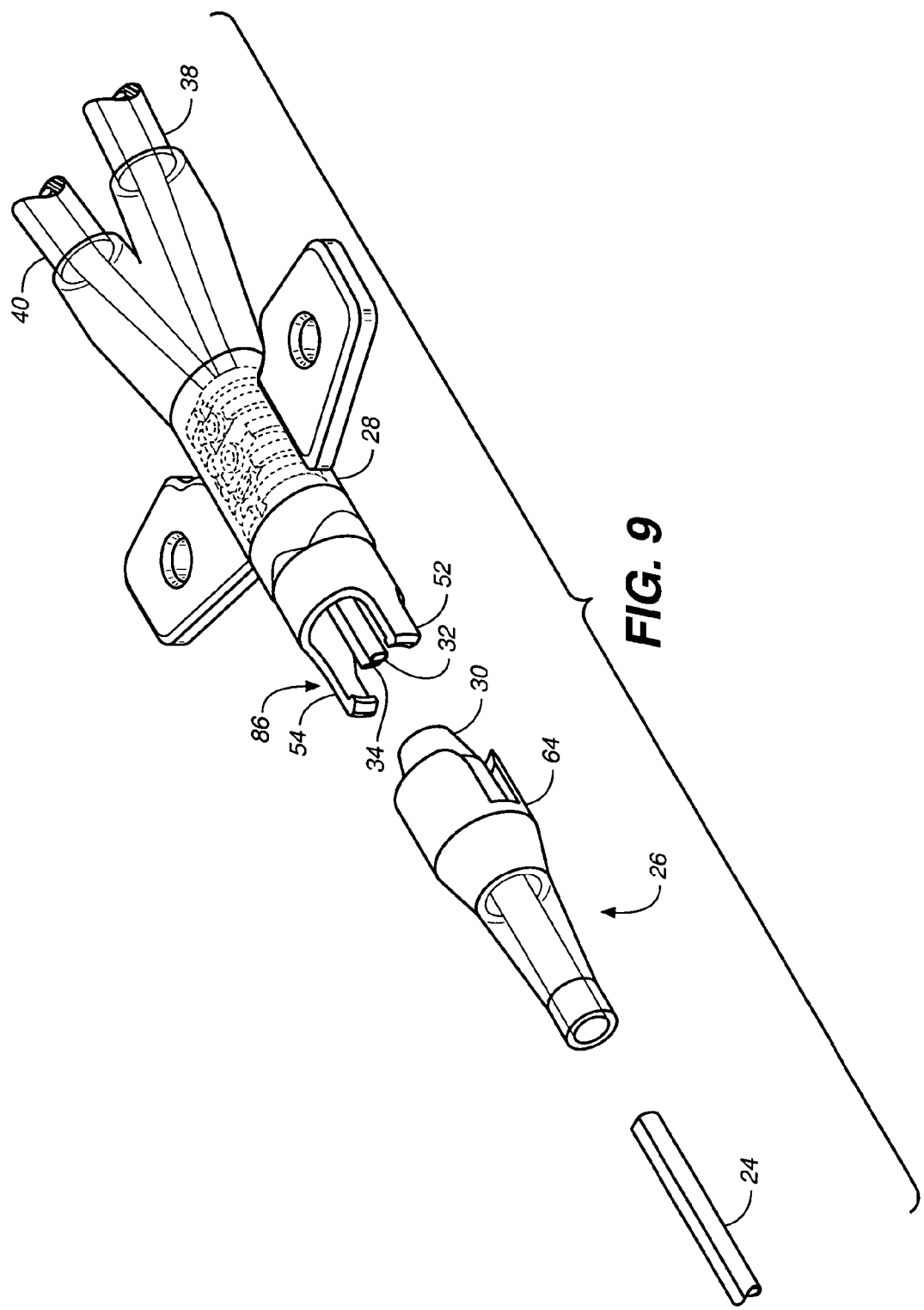

This design eliminates the need for a free-floating compression member. The soft collet provides compression to retain the catheter on the cannula while protecting the soft catheter material from any potential sharp edges or hard surfaces of the hard over-sheath. In one variation the soft collet comprises a polymer within Durometer in the range of about 30-100 Shore A. In another variation, the soft collet comprises silicone of about 40-60 Shore A. In another variation, the soft collet comprises silicone of about 40-50 Shore A. In yet another variation, the soft collet comprises a polymer of about 80 Shore A. Also, the cut-away portion 86 of the bifurcation's distal interface, between the snap-lock arms 52, 54, allows the user to visually confirm that the catheter tubing 24 is properly loaded onto the cannula 32, 34, as shown in FIG. 9. Finally, the connection of the snap-lock arms 52, 54 onto the hard over-sheath 64 provides a positive snap, indicating to the user that connection has been achieved.

The catheter may be used for facilitating the introduction or removal of a fluid to or from a body. In one variation, the proximal end of the catheter connector hub (e.g., bifurcation, etc.) is temporarily attached to a luer fitting connector of an extension catheter. In another variation, the proximal end of the catheter connector hub is permanently attached to the extension catheter in lieu of the luer fitting connection. In yet another variation, the catheter connector hub is coupled to an extension catheter, which is utilized for chronic excess fluid drainage from a body. In another application, the catheter connector hub is coupled to an electromechanically powered and/or magnetically coupled vesicular pump to permit assisted flow of a fluid into or out of a body. This flow may be uni-directional or bi-directional.

Figure 10:
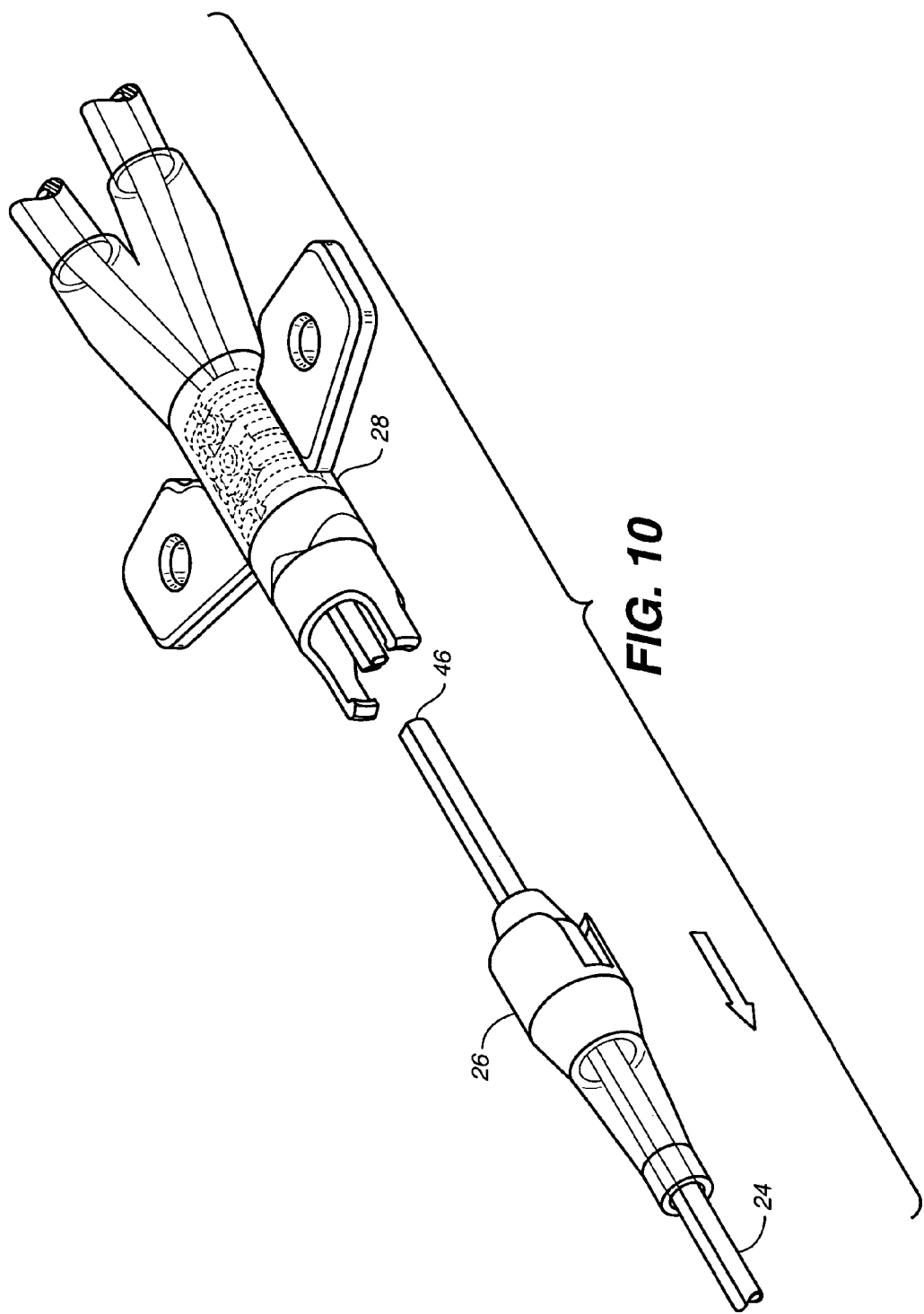

One exemplary method for utilizing the catheter connector system to establish fluid communication with a patient's circulatory system comprises attaching a bifurcation to an implanted catheter according to the procedure described below. The user is provided with a catheter 24, a connector sheath 26, and a bifurcation 28, as shown in FIG. 9. The connector sheath 26 comprises a soft collet 30 positioned within a hard over-sheath 64. The bifurcation 28 comprises two distally-extending cannulas 32, 34, and extension legs 38, 40 extending in the proximal direction. The distal portion of the catheter 24 is first inserted into the patient's circulatory system through methods that are well known to one of ordinary skill in the art. Once the catheter is properly positioned, the proximal portion of the catheter outside the patient's body is trimmed to the desired length. The connector sheath 26 is then slid over the proximal portion of the catheter 24 as shown in FIG. 10. If the user feels some resistance while advancing the connector sheath 26, the user may gently twist back and forth or spin the connector sheath to ease its passage over the catheter.

Figure 11A:
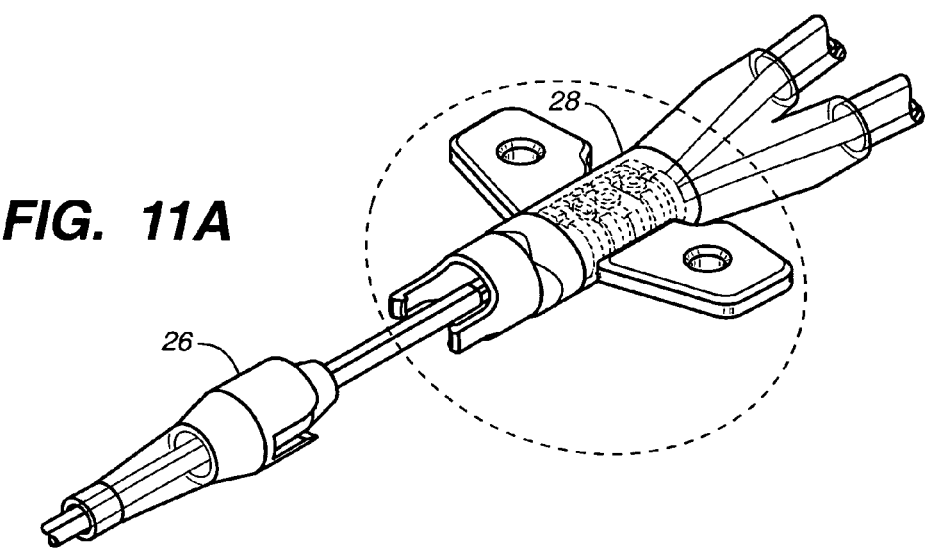
FIG. 11A illustrates the cannulas on the bifurcation being inserted into the lumens of the catheter.
Figure 11B:
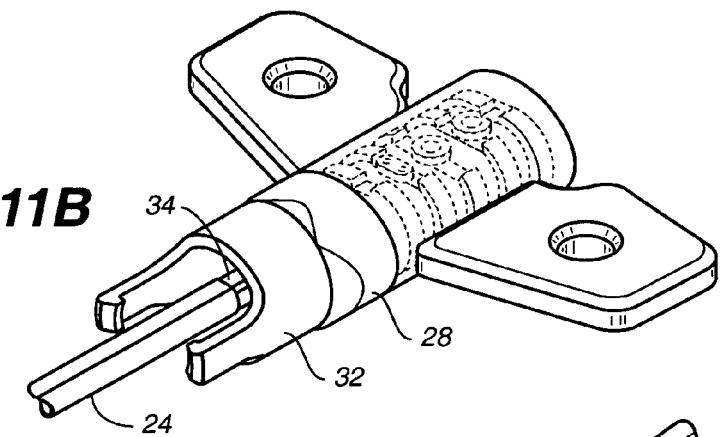
FIG. 11B is an expanded view of FIG. 11A showing the cannula inserted within the lumens of the catheter.
Figure 12:
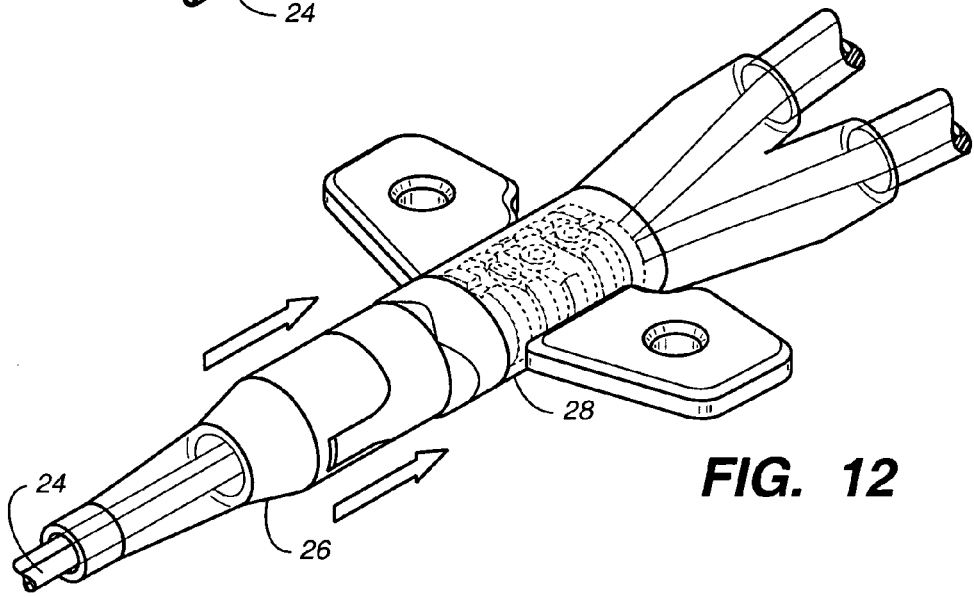

While ensuring that the lumens of the catheter 24 are aligned with the two distally extending cannulas 32, 34, the user then advances the catheter 24 onto the cannulas 32, 34 until the proximal end 46 of the catheter is abutting the body of the bifurcation 28, as shown in FIGS. 11A and 11B. The catheter 24 is adjusted, if necessary, such that it lies parallel with respect to the cannulas 32, 34 without any kinks. With a straight motion, the user then slides the connector sheath 26 in the proximal direction to engage the distal interface on the bifurcation 28, taking care to align the slots/grooves on the hard over-sheath of the connector sheath with the snap-lock arms on the distal interface of the bifurcation, as shown in FIG. 12. The user then advances the connector sheath completely until the connector sheath and the bifurcation are fully attached. A tactile, locking sensation and/or an audible click confirms that the two pieces are properly engaged.

This invention has been described and specific examples of the invention have been portrayed. While the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. Therefore, to the extent there are variations of the invention, which are within the spirit of the disclosure or equivalent to the inventions found in the claims, it is the intent that this patent will cover those variations as well.

What is claimed as new and desired to be protected by Letters Patent of the United States is:

1. A catheter connector system, comprising:
    a catheter;
    a connector sheath comprising a soft collet and a hard collet sheath, wherein the soft collet extends both proximally and distally beyond the hard collet sheath, and wherein the soft collet includes a lumen sized for slidable positioning over at least a proximal end of the catheter; and
    a connector hub comprising a cannula sized for insertion into a lumen of the catheter and a distal interface with a cavity for receiving at least a portion of the soft collet, a proximal portion of the cavity configured to directly contact the soft collet and compress the soft collet against the proximal end of the catheter;
    wherein one of the connector hub or the hard collet comprises at least one distally extending lock arm and the other comprises at least one external lock slot, wherein the at least one distally extending lock arm and the at least one external lock slot are configured to engage each other,
    wherein the connector hub is secured to the connector sheath by aligning the at least one distally extending lock arm and the at least one external lock slot and moving the connector sheath and the connector hub together in a straight motion with respect to the axis of the catheter until the at least one distally extending lock arm and the at least one external lock slot are locked together.

2. The catheter connector system according to claim 1, wherein the connector sheath is a unitary connector sheath with the hard collet sheath and the soft collet fixedly attached together.

3. The catheter connector system according to claim 1, wherein a wall forming the cavity is tapered such that the cross-section of the cavity is larger at a distal end than at a proximal end thereof.

4. The catheter connector system according to claim 1, wherein the catheter comprises a D-shaped lumen and the cannula includes a non-circular cross-section configured for engaging a wall of the D-shaped lumen.

5. The catheter connector system according to claim 1, wherein the cannula comprises a metallic material.

6. The catheter connector system according to claim 1, wherein the catheter comprises a dual lumen catheter and the connector hub comprises a bifurcation including two cannulas.

7. The catheter connector system according to claim 6, wherein a proximal portion of the cannulas are angled away from each other.

8. The catheter connector system according to claim 7, further comprising two extension legs connected to a proximal end of the cannulas.

9. The catheter connector system according to claim 6, wherein the bifurcation comprises a hard core molded over the two cannulas, and a soft overmold positioned over the hard core.

10. The catheter connector system according to claim 9, wherein the cannulas comprise a metallic material.

11. The catheter connector system according to claim 10, wherein the catheter comprises two D-shaped lumens, each of the cannulas including a non-circular cross-section configured for establishing a seal with the D-shaped lumens.

12. The catheter connector system according to claim 11, wherein the cannulas comprise a metallic material.

13. The catheter connector system according to claim 1, further comprising:
    means for generating an audible notification to an user when the at least one distally extending lock arm or the at least one lock slot of the hard collet engages with the at least one distally extending lock arm or the at least one lock slot of the connector hub.

14. A multi-lumen catheter connector, comprising:
    a multi-lumen catheter;
    a unitary connector sheath comprising a soft collet and a hard collet sheath, wherein the hard collet sheath is fixedly retained to the soft collet, and wherein the proximal end and the distal end of the soft collet extend beyond the hard collet sheath; and
    a connector hub comprising a plurality of cannulas corresponding to the number of lumens in the multi-lumen catheter, wherein the plurality of cannulas are configured for insertion into a proximal end of the multi-lumen catheter, and wherein the connector hub comprises a cavity for receiving the soft collet, the cavity being configured to compress the proximal end of the soft collet against the proximal end of the multi-lumen catheter, the proximal end of the soft collet that extends beyond the proximal end of the collet sheath being configured to directly contact the connector hub;
    wherein one of the connector hub or the hard collet comprises at least one distally extending lock arm and the other comprises at least one external lock slot, wherein the at least one distally extending lock arm and the at least one external lock slot are configured to engage each other,
    wherein the connector hub is secured to the connector sheath by aligning the at least one distally extending lock arm and the at least one external lock slot and moving the connector sheath and the connector hub together in a straight motion with respect to the axis of the catheter until the at least one distally extending lock arm and the at least one external lock slot are locked together.

15. The catheter connector according to claim 14, wherein a distal portion of the connector hub further comprises a cut-out portion, permitting visual observation of the cannula during insertion into the catheter.

16. The catheter connector according to claim 14, wherein each of the cannulas comprises a distal end, a mid-section, a proximal portion, and a proximal end, wherein the proximal portions of the cannulas are angled away from each other.

17. The catheter connector according to claim 16, wherein each of the cannulas includes a lumen with an expanding proximal portion that provides a smooth transition between a plurality of extension legs connected to the proximal ends of the cannulas and the lumens within the catheter.

18. The catheter connector according to claim 16, wherein the connector hub further comprises an overmold positioned over at least the mid-sections of the cannulas, a plurality of extension legs connected to the proximal ends of the cannulas, and a plurality of luer connectors attached to the extension legs.

19. The catheter connector according to claim 14, wherein each cannula includes a metal tubing.

* * * * *